United States Patent
Liem et al.

(10) Patent No.: US 6,632,439 B2
(45) Date of Patent: Oct. 14, 2003

(54) FUSOBACTERIUM NECROPHORUM VACCINE AND METHOD FOR MAKING SUCH VACCINE

(75) Inventors: Adrian Liem, Lenexa, KS (US); Gary A. Anderson, Bucyrus, KS (US); Douglas L. Stine, Olathe, KS (US)

(73) Assignee: Novartis Animal Health, Inc. (CH)

( * ) Notice: Subject to any disclaimer, the term of this patent is extended or adjusted under 35 U.S.C. 154(b) by 0 days.

(21) Appl. No.: 09/408,328

(22) Filed: Sep. 29, 1999

(65) Prior Publication Data

US 2002/0114817 A1 Aug. 22, 2002

(51) Int. Cl.[7] ................ A61K 49/00; A61K 39/395; A61K 39/40; A61K 39/00; A61K 39/38
(52) U.S. Cl. ............... 424/234.1; 424/9.2; 424/130.1; 424/164.1; 424/178.1; 424/184.1; 424/197.11; 424/234.1; 424/278.1; 424/282.1; 435/243; 435/252.1; 435/253.6; 435/2; 935/65
(58) Field of Search ................ 424/9.2, 130.1, 424/164.1, 178.1, 197.11, 823, 824, 184.1, 234.1, 278.1, 282; 435/243, 252.1, 253.6; 935/65

(56) References Cited

U.S. PATENT DOCUMENTS

| 5,455,034 A | * 10/1995 | Nagaraja et al. | 424/236.1 |
| 5,492,694 A | * 2/1996 | Nagaraja et al. | 424/236.1 |
| 5,861,162 A | 1/1999 | Nagaraja et al. | 424/203.1 |

FOREIGN PATENT DOCUMENTS

| EP | 460480 | * 12/1991 | A61K/35/74 |
| EP | 0460480 B1 | 1/1996 | A61K/35/74 |
| RU | 2043770 | * 2/1993 | |

OTHER PUBLICATIONS

Tan et al. 1992. Vet. Micro. 32: 15–28.*
Boslego et al. 1991. Vaccines and Immunotherapy. Chapter 17, pp. 211–223.*
J. Vet Diagn Invest 5:282–283 (1993) Outer membrane proteins of *Fusobacterium nectophorum* biovars A, AB and B: their taxonomic relationship to *F. necrophorum* subspecies *necrophorum* and *F. necrophorum* subspecies *funduliforme*; Patrica C. Ainsworth, Charles M. Scanlan.
Veterinary Microbiology, 32 (1992) 15–28, Elsevier Science Publishers B.V., Amsterdam; Factors affecting the leukotoxin activity of *Fusobacterium necrophorum* [1]; Z.L. Tan[a], T.G. Nagaraja[a] and M.M. Chengappa[b]; pp. 15–28.
Am J. Vet Res, vol. 47, No. 7, Jul. 1986; Biochemical characterization of the keukotixins of three bovine strains of *Fusobacterium necrophorum*; C.M. Scanlan, DVM, Ph.D.; J.N. Berg, DVM, Ph.D.; F.F. Campbell, BS; pp. 1422–1425.

* cited by examiner

Primary Examiner—Lynette R. F. Smith
Assistant Examiner—JaNa Hines
(74) Attorney, Agent, or Firm—Michael Lee; David L. Marks

(57) ABSTRACT

The present invention relates to a method of producing a vaccine for the prevention of *F. necrophorum* bacterial infections, comprising isolating the *F. necrophorum* bacteria from a bovine species, growing the bacteria in a suitable growth medium for a period equal to between about 10 hours and about 18 hours so as to achieve a bacterial population equal to at least $1 \times 10^5$ CFU/ml, terminating the growth, and using a whole cell culture to form the vaccine. Additionally, the present invention relates to the vaccine comprised of a killed whole cell population of the *F. necrophorum* bacteria taken from a bovine. The present invention further relates to a method for preventing footrot and liver abscesses caused by *F. necrophorum* bacteria.

1 Claim, No Drawings

FUSOBACTERIUM NECROPHORUM VACCINE AND METHOD FOR MAKING SUCH VACCINE

FIELD OF INVENTION

The present invention relates to a vaccine, and an in-vitro method for developing such a vaccine, for establishing resistance to *Fusobacterium necrophorum* bacteria that is responsible for footrot and liver abscesses in the bovine species.

DESCRIPTION OF THE PRIOR ART

The infectious disease "footrot" is caused by colonization of *F. necrophorum* bacteria and typically occurs when the colonization locates in the area of a trauma site to the foot followed by exposure to a wet and slushy environment. The disease most commonly occurs in cattle and sheep, with the disease, usually acute, being characterized by painful inflammation of the interdigital skin of the infected subject. Outward characterizations of the footrot disease include lameness in one or more legs, loss of appetite, loss of weight, and occasional mortality.

In cattle, the *F. necrophorum* bacteria that causes footrot may also cause liver abscesses. The etiological pathway for such an *F. necrophorum* infection leading to liver abscesses is different than that associated with footrot. When *F. necrophorum* induced liver abscess occurs in ruminants, especially cattle, it typically is the result of a pathway provided to the bloodstream by an ulcerated rumen (stomach), through which pathway the *F. necrophorum* bacteria, otherwise indigenous as a microflora present in the gastro-intestinal tract, passes. Once in the bloodstream, the bacteria continue through the portal vein and invade the liver causing abscesses.

Because of the severe economic losses caused to the cattle industry by footrot and liver abscess diseases, there is a need for an easily administered vaccine for cattle that readily inhibits propagation of *F. necrophorum* bacteria. Such a vaccine is most desirable if it establishes optimal resistance in inoculated members to reduce the number of instances of footrot and liver abscesses in cattle.

Conventional vaccines use various killed strains of *F. necrophorum* bacteria including, for example, the biotype A strains [*F. necrophorum* subspecies *necrophorum* (FNN)], to prevent footrot, liver abscesses, and other infectious diseases resulting from colonization by the bacteria. While conventional vaccines experience some degree of success in preventing colonization and infection with the *F. necrophorum* bacteria, suitable prevention and inhibition of colonization and infection by the bacteria in cattle is still lacking for various reasons. First, some conventional vaccines are derived from a bacteria colony supernatant created from the physical separation of a bacteria colony grown in-vitro from its growth media. It is important and desirable, therefore, that after the separation is complete, the supernatant from which the vaccine is generated, contain certain key proteins. The physical separation process, however, typically separates antigenic proteins found in the growth media from the supernatant used to generate the vaccine. If for any reason, key bacterial proteins are removed from the supernatant during separation—which can occur if such key proteins are in the form of solids which do not remain suspended in liquid, then a vaccine created from the supernatant will necessarily lead to a non-optimum antigenic response in the vaccinated animal. Conventional vaccine production methodologies typically produce vaccines which do not illicit a maximum antigenic response in an inoculated host because of this undesirable method.

The reduction of a vaccine's antigenic response from optimal to insufficient can be brought about by the internal physical stresses imposed on the bacterial cell structure by centrifuge techniques used to separate the bacteria initially suspended in its liquid growth media. Centrifuge-induced stress imposed on the bacteria cells can result in undesirable detachment or division of cell components from the remaining bacteria cell structure. Thus, if the cell wall, for example, ruptures—permitting the cell contents to flow out of the cell wall, then the solid but damaged cell wall will, as part of the separation process, settle as a solid from the supernatant created by the centrifugation process and used to form the vaccine. Any antigenic properties associated with the cell wall will, thus, be lost, producing a less than optimal immune response to the vaccine.

A less than optimum immune response to conventional vaccines also occurs in cattle vaccine production methodologies using bacteria strains isolated from host members other than cattle. For example, a vaccine derived from bacteria isolated from sheep may cause less than a full immune response in cattle because the phenotypic characteristics of the particular bacterial strain derived from sheep may be slightly different than that associated with strains obtained from cattle.

It has also been discovered that the efficacy of a vaccine can be negatively influenced by harvesting the in-vitro bacterial culture during an inappropriate time frame within the bacterial culture growth phase. As a bacterial culture grows and matures, certain desirable proteins, important for vaccine production, are produced in greater quantities during certain phases of culture growth.

Turning now to certain specific prior art patents relating to the present invention, U.S. Pat. Nos. 5,455,034 ('034) and 5,492,694 ('694) to Nagaraja et al. disclose a *Fusobacterium necrophorum* leukotoxoid vaccine derived bacteria grown for a maximum of 10 hours, preferably 6–9 hours, while maintaining the culture pH in a range between 6.5 and 8, in order to maximize the production of leukotoxin—a specific protein generated by the bacteria. The leukotoxin supernatant is separated from the bacteria and inactivated for use in the vaccine. The leukotoxin protein is specifically isolated and the rest of the bacterial culture is discarded, with only a specific portion of the bacterial culture used to form the vaccine. The '694 Patent thus discloses a vaccine production methodology in connection with which bacterial cultures are grown for specific periods of time, after which very specific portions of the bacterial culture are isolated. In the '034 Patent, a vaccine production methodology is disclosed in which an inactivated cell culture product of *Actinomyces pyogenes* was added as an additional component.

In European Patent EP0460480, entitled Bacterin for the Treatment of *necrophorum* Diseases and a Method for the Production Thereof, invented by Berg, a method is disclosed that uses whole-cell suspensions of *F. necrophorum* which have been inactivated using β-propiolactone (BPL). The patent further discloses a method whereby the bacteria are cultured until fermentation is complete, which is approximately 18 hours or greater. The longer fermentation period is believed to result in the enzymatic breakdown of various proteins that may be important to the efficacy or antigenic properties of the vaccine. Also, the isolate used is derived from an ovine species as opposed to a bovine, which is likely less effective in cattle than an isolate from a bovine species.

A problem associated with the Berg patent is that it requires a higher dosage of vaccine to be administered to a subject. The higher vaccine dosage–2 to 6 ml, increases the chances of lesions forming at the inoculation point.

For the above reasons, there is a need for a vaccine which induces an optimal immune response in an inoculated host to substantially prevent diseases such as footrot or liver abscesses. It is also desired to have a vaccine that can be administered in smaller dosages so that the chances for lesion formation at the inoculation point is lessened. Such a vaccine should be economical to produce, as many known methods for forming the vaccines require numerous steps and expensive equipment.

SUMMARY OF THE INVENTION

The present invention relates to a vaccine, and method for forming the vaccine, for administration to ruminants, most preferably bovines, for establishing resistance to infectious diseases of footrot and liver abscesses caused by the *F. necrophorum* bacteria. The present inventive vaccine comprises a killed whole cell culture of the *F. necrophorum* bacteria, which prior to killing was grown in its last generation for at least 10 hours until attaining a bacterial population count equal to at least $1 \times 10^5$ CFU/ml. Importantly, the vaccine is comprised of a killed whole culture of the *F. necrophorum* bacteria which was derived from an isolate taken from a member of the bovine species. Also, the present invention relates to a method for preventing diseases in ruminants, especially cattle, such as footrot and liver abscesses caused by *F. necrophorum*.

In the method for forming the vaccine, an *F. necrophorum* bacterial isolate is taken from a ruminant species member and, more preferably, from a bovine species member. Additionally, the *F. necrophorum* bacteria are preferably a biotype A (FNN) isolate. To form a sufficient amount of vaccine, the isolate is grown in multiple generations, with typically about eight (8) generations or passages of the isolate grown to generate a commercially sufficient amount of bacteria. Any anaerobic media that supports suitable growth of the isolate into a sufficient population to form a vaccine can be used. Each bacterial generation is preferably grown for a period of time equal to between about 10 hours and about 18 hours. Importantly, the final bacterial generation is grown for a period of time sufficient to result in a population equal to at least $1 \times 10^5$ CFU/ml and, more preferably, $1 \times 10^8$ CFU/ml, and for a period of time sufficient for the bacteria to generate a desired antigenic response in an inoculated host. Certain proteins, antigens, and other cellular products are produced by the bacterial population with the passage of time.

At certain times the desirable cellular products will be present in greater quantities than at other times. Once formed, such cellular products may break-down with the passage of time. As such, the desired cellular products that illicit the preferred immune response are believed present in the time period ranging between ten (10) and eighteen (18) hours of the last generation.

Once the bacterial culture has grown for a sufficient period of time and reached a sufficient population, the growth of the culture is terminated. Preferably, formaldehyde is used to terminate growth. The growth terminated whole bacterial cell culture, is available for use as a vaccine with it noted that the whole cell culture is most preferred for use as a vaccine as opposed to a portion of the bacterial culture.

The whole cell culture can be mixed with an amount of diluent, including adjuvants and saline solution or filler. An adjuvant is preferred because it allows for the delivery of a more antigenically effective amount of the whole cell culture. Generally, the adjuvant allows for the use of a lesser amount of the bacterial culture in the vaccine. The most preferred adjuvant is oil based.

The method for preventing pathogenic manifestations of the *F. necrophorum* bacteria, such as footrot and liver abscesses, involves forming the vaccine from a whole cell culture derived from an *F. necrophorum* bacteria isolate preferably taken from a bovine species and administering a sufficient amount of the vaccine to the inoculated subject. The amount of vaccine administered to establish optimal resistance is primarily dependent upon the amount of bacteria in the killed whole cell culture. If an adjuvant is used, the vaccine amount will also depend upon the particular adjuvant selected for use. Preferably, the vaccine is administered at least once in an amount equal to between 1 ml and 5 ml.

The present invention addresses a perceived problem of an inadequate immune response in known commercially available vaccines used in the prevention of the diseases footrot and liver abscesses caused by infection of *F. necrophorum* bacteria. The present invention provides a vaccine that causes a believed improved antigenic response in inoculated ruminants, and especially in bovines. By growing the bacteria for multiple generations and the specified times, particularly desirable proteins produced by the bacteria achieve greater levels in the culture. This, in turn, provides a more effective vaccine against *F. necrophorum*. Isolation of the seed bacteria from a bovine species is believed to further enhance the antigenicity of the vaccine. Inactivating the cultures with formaldehyde allows for improved preservation of the killed bacteria, and using an adjuvant whose characteristics allow for maximum titer of the bacteria in the vaccine, as well as maximum ease with which the vaccine can be administered in the field, also contributes to the efficacy of the vaccine. The improved vaccine may be administered in smaller doses, thereby reducing the risk of lesions forming at the inoculation point. Thus, the present invention provides a believed improved antigenic response against *F. necrophorum* infections without an attendant increase in the risk of lesions in the inoculated subject.

DETAILED DESCRIPTION

The present invention relates to the production of an effective vaccine for the immunization of ruminants, especially bovines or cattle, against *Fusobacterium necrophorum* bacterial infections. More particularly, the present invention relates to a method for forming a vaccine from a killed whole cell *F. necrophorum* bacterial culture isolated originally from a bovine member and cultured for at least 10 hours. This in turn relates to a method for preventing pathogenic manifestations, or diseases such as footrot and liver abscesses, in a ruminant resulting from infection with the *F. necrophorum* bacteria. Advantageously, because the vaccine is derived from a whole cell culture, the vaccine will include all the antigens or protein products or cell products produced by a bacterial population that are believed to be critical to the induction of an effective immune response in an inoculated host organism.

The method for producing the vaccine is initiated by expressing any isolate of *F. necrophorum* bacteria. It is preferred that the isolate of *F. necrophorum* be virulent and obtained from a bovine. The isolate could be obtained from other host organisms, in particular other ruminants, but it is most preferred for the isolate to be taken from a bovine. To ensure optimum vaccine antigenicity, in accordance with the invention, a virulent strain of *F. necrophorum* bacteria is chosen for vaccine production. Determination of virulence can be made where a host organism exhibits acute signs of infection. The *F. necrophorum* bacteria can be biotype A (FNN), B [*F. necrophorum* subspecies *funduliforme* (FNF)], or AB (FNN), any of which strain is believed to be available as an isolate for use in forming the present vaccine. More preferably, biotype A (FNN) *F. necrophorum* bacteria is selected because it tends to be the most virulent which will, in turn, most likely cause the strongest immune response when introduced into a host as a vaccine. In the most preferred method, the strain of *F. necrophorum* bacteria used is obtained from a bovine and identified as strain number 021496, ATCC No. PTA-917.

After the isolate is obtained, it should be tested to ensure that it is not contaminated and that the isolate is biologically pure. The isolate may then be used immediately or stored prior to culturing. If the isolate is to be stored prior to culturing, it is preferred that it be stored at a temperature ranging between about 2° C. and about 7° C. or any temperature that sufficiently preserves the isolate without destroying it.

Because the isolate taken from the infected subject does not comprise a sufficient quantity of bacteria to form a vaccine, it is necessary to culture in-vitro the bacterial isolate for a number of generations or passages to increase the bacteria or isolate population. The bacteria can be grown in any suitable growth medium known to support population expansion of the *F. necrophorum* or any other similar type of bacteria species. Generally, any rich medium can be used such as blood agar, chocolate agar, meat digests, and brain heart infusion, for example. The preferred growth medium is Brain Heart Infusion Broth, and the most preferred growth medium is Brain Heart Infusion Broth supplemented with yeast extract, L-Cysteine HCL, and resazurin. Also, it is preferred to express the bacteria under anaerobic conditions.

In order to maximize the immune response achieved by the administered vaccine, the bacteria should be grown in-vitro for a time sufficient to allow the production of all antigens, proteins, or cellular products necessary to induce an improved immune response in the inoculated subject. In accordance with the invention, the specific antigens produced are not necessarily identified, it is only known that the best immune response is achieved. To ensure that the desired immune response is achieved, the bacterial culture should achieve a sufficient population and be harvested at a particular time. The optimal time is not necessarily determined on the basis of population; instead, it is based upon the need to establish a level of cell products and proteins in the culture. In the preferred method, such products and proteins are optimally produced when the bacterial population is grown in the culture medium until an optical density of at least 0.4 at 540 nm is observed on a spectrophotometer, which corresponds to about $1 \times 10^5$ CFUs/ml of the bacteria. In the most preferred method, the bacteria are grown until an optical density of at least 0.8 at 540 nm is observed on a spectrophotometer, which corresponds to about $1 \times 10^8$ CFUs/ml. Any amount of bacterial isolate can be used so long as a sufficient population exists to form a vaccine. Also, if additional bacterial generations are grown—thereby increasing the population to a point beyond that needed to form a vaccine, this is not a problem, as the population can be diluted when forming the vaccine. Thus, the bacterial population should equal at least $1 \times 10^5$ CFUs/ml.

The time necessary to achieve a sufficient population and amount of cellular product will generally be equal to a culture growth period of at least 10 hours in the harvested generation. This is the culture growth time of the last generation that is to be used to form the vaccine. Typically, the time will be equal to between greater than 10 hours and less than 18 hours. More preferably, the growth period will range between about 11 hours and about 14 hours, with 12 hours the most preferred. The temperature for growing the bacteria will typically range between about 33° C. and about 40° C. More preferably, the bacteria growth temperature will range between about 35° C. and about 38° C. However, it is understood that the culturing conditions can be varied to achieve the same result and still fall within the scope of this invention.

In order to obtain a sufficient sample size for production of the vaccine, it is possible to passage the bacteria several times into successively larger volumes of fresh culture medium until the desired volume of the bacteria culture is achieved. In the preferred method, the bacteria are passaged no more than eight (8) times. The number of passages is primarily attributable to compliance with various United States Department of Agriculture (USDA) regulations.

In the most preferred method for forming a sufficient bacterial culture for use in a vaccine, the bacteria isolate is inoculated into the culture medium of brain heart infusion in a 100 mL flask and grown for between about 14 and about 18 hours at a temperature ranging between 35° C. and about 38° C. The bacterial culture is then passaged into fresh media in a 1L flask and grown for between about 14 and about 18 hours at a temperature ranging between about 35° C. and about 38° C. This procedure is repeated until it is determined that a sufficient volume of culture is present to sustain a production culture. Production cultures are then grown in culture vessels for about 10 to about 18 hours at a temperature ranging between about 35° C. and about 38° C.

The growth of the bacterial culture should be monitored regularly. Growth of the bacteria can be monitored by any known method for accurately calculating the growth of the bacteria. In the preferred method, growth of the bacteria is both observed with the naked eye and measured under a spectrophotometer. The spectrophotometer can be calibrated to any known acceptable wavelength for accurately measuring bacteria growth. In the preferred method, the spectrophotometer is calibrated to 540 nm.

Termination of growth can be achieved using any method known to effectively terminate the growth of *F. necrophorum* bacteria or other similar bacteria while not significantly altering the protein or cellular products found within the bacterial culture. It is believed especially important not to use a method of terminating bacteria growth that will affect the bacteria cell wall integrity. Examples of suitable compositions for terminating growth include β-propiolactone, gluteraldehyde, and formaldehyde. In the preferred method, formaldehyde is used to terminate the growth of the bacteria because formaldehyde is believed to best maintain the antigenicity of the cell culture. It is hypothesized that the formaldehyde may in fact stabilize the antigens found in the cell culture. In the most preferred method, a 37% formaldehyde solution is used in an amount equal to about 0.4% by volume of the bacterial culture. Obviously, other amounts of formaldehyde or growth inactivating agent can be used.

The inactivated whole cell culture may be used immediately for production of a vaccine, or it may be stored prior to production. Regardless, the whole cell bacterial culture is then harvested using any technique known to be sufficient to recover at least $1 \times 10^8$ CFUs/ml e.g. (pipetting the culture out of the flask or device in which the culture was grown).

The harvested whole cell culture can then be used as a vaccine or can be mixed with a diluent. A combination of diluent and the whole cell culture can still function as an improved vaccine, but will be referred to herein as a vaccine inoculum. It is known that the whole cell culture could alone be used as the vaccine; however, it is preferred to mix the culture with a diluent, for, among other reasons, cost effectiveness.

The diluent can be any of a variety of compositions including, but not limited to, adjuvants, fillers, and combinations thereof. Most preferably, the vaccine is comprised of the whole cell bacterial culture and a diluent which includes an adjuvant and a filler. A wide range of adjuvants can be used, with the adjuvant being any adjuvant known to be effective in maintaining a high titer of bacteria in the vaccine and to be easily syringeable, as well as, exhibiting other characteristics which make it practical for use in a vaccine which will be administered in the field year-round. It is important that the adjuvant can hold a quantity of inoculum equal to at least $1 \times 10^5$ CFUs/ml of the bacteria. Adjuvants are compositions which are used to hold (or carry) a titer of bacteria, with the adjuvants used to partly maintain the efficacy of the antigens associated with the bacteria by slowly releasing them in the host after vaccination. Representative examples of suitable adjuvants are aluminum salts, such as aluminum hydroxide and aluminum phosphate; polymers, such as POLYGEN[1], DEAE dextran, dextran sulfate, and methyacrylates; dimethylo-decylammonium bromide; poxvirus proteins, such as [B]baypamune; [A]avirdine, Lipid A; oils, such as EMULSIGEN®, EMULSIGEN PLUS[2], SuprImm®[3]; animal oils, such as squalane or squalene; mineral oils, such as [Drakeol]DRAKEOL®[4] and [M]montanides; vegetable oils, such as peanut oil; block co-polymers; triterpenoid glycosides, such as saponin, QuilA, and QS21; detergents, such as such as Tween-80 and Pluronic[5], bacterial component adjuvants, such as Corynebacterium, Propionibacterium, and Mycobacterium; interleukins, monokines, and interferons; liposomes; ISCOMs; synthetic glycopeptides, such as muryamyl dipeptides and derivatives thereof, cholera toxin; or combinations of the above. More preferably, the adjuvant is selected from the group consisting of oils, aluminum salts, polymers, dimethyldeodecylammonium bromide, poxvirus proteins, block co-polymers, triterpenoid glycosides, detergents, and combinations thereof. Most preferably, the adjuvant is an oil-based adjuvant, and in the most preferred method the adjuvant is an oil-based adjuvant which is produced under the name of [SuprImm]®SUPRIMM oil, which is manufactured by ImmTech Biologics, LLC, Bucyrus, Kans. 66013.

1. POLYGEN is a trademark of Modern Veterinary Products corp. Of Omaha, Nebr.
2. EMULSIGEN® and EMULSIGEN PLUS are trademarks of Modern Veterinary Products of Omaha, Nebr.
3. SUPRIMM® is a trademark of Immtech Biologics, Inc. of Bucyrus, Kans.
4. DRAKEOL® is a trademark of Pennzoil Products, Corp., of Houston, Tex.
5. Pluronic is a trademark of BASF Corp. Of Parsippany, N.J.

The adjuvant can be present in the vaccine inoculum in any amount determined to be sufficient to maintain a high titer of the bacteria. In the preferred method, the adjuvant is present in the vaccine inoculum in an amount equal to between about 10% and about 30% by volume of the whole cell bacterial culture. More preferably, the adjuvant is present in an amount ranging between about 18% and about 24% by volume of the whole cell bacterial culture.

The fillers used as part of the diluent can be any of a variety of compositions which do not negatively influence the vaccine and which can be used to economically dilute the vaccine. A preferred filler is a saline diluent or saline solution. The saline solution can be added in an amount which is sufficient to form a viable solution for transmission of the vaccine when administered.

Once formed, the vaccine can be administered to any ruminant—but is preferably administered to a bovine, by any conventional procedure known, such as an intramuscular or subcutaneous injection. The subcutaneous injection is preferred because it is less likely to cause injection site lesions. The appropriate dosage of vaccine is determined primarily by the amount of bacteria and the antigenicity of the culture found in the vaccine. As such, any reasonable amount can be administered, with it being preferred that the dosage be 1 ml and 5 ml. A dosage of 2 ml is even more preferred. The smaller doses are preferred because they lessen the chance of lesions forming on the inoculated subject species. It is also preferred that a booster vaccination be administered at a time equal to between about 2 and about 13 weeks, after the primary vaccination, and preferably 3 weeks after the primary vaccination.

Thus, the present invention relates to a method for producing a vaccine that is able to induce an improved immune response against *F. necrophorum* infections by utilizing a whole-cell culture of the bacteria that has been grown until the desired level of all antigens and/or proteins has been reached. The culture is inactivated and preferably combined with an adjuvant that is able to carry an appropriate quantity of bacteria in the vaccine and is easily syringeable. This permits use of a smaller dosage which, in turn, helps to reduce the risk of lesions forming at the inoculation point. Field studies have demonstrated that the vaccine is effective in reducing the incidence of both footrot and liver abscesses in cattle, two pathogenic effects of *F. necrophorum* infection.

The following examples are for illustration purposes only and are not meant to limit the claims in any way.

EXAMPLES

Example 1

A method for forming a vaccine to be used to inoculate cattle and prevent infection by an *F. necrophorum* bacteria was performed. Primarily, the method related to formation of a vaccine prior to administration to a bovine.

The method for forming the vaccine was initiated by obtaining a sample of *F. necrophorum* bacteria, previously isolated from cattle, from Dr. C. M. Scanlan, Texas A&M University, and identified as *F. necrophorum* strain number 021496. The sample, which was a lyophilized culture and was stored at 2–7° C. in a refrigerator until it was ready to be used. Next, the lyophilized cultures were grown on streaked agar blood plates (1–2 plates) and incubated at 37° C. for 20 hours to confirm purity of the culture.

From the blood plates, a culture of *Fusobacterium necrophorum* was isolated and added to a pre-reduced Brain Heart Infusion Broth (BBL, Difco, Oxoid, Remel, or equivalent) supplemented with 0.5% by weight Yeast Extract, 0.05% by weight L-Cysteine HCL, and 1 ml/L resazurin (0.025% sol.). The medium was purchased as a dry powder and prepared according to the manufacturer's instructions. Production cultures were grown anaerobically until a bacterial count of $3 \times 10^8$ CFU/ml was reached, indicated by an optical density of 0.8 at 540 nm using a spectrophotometer manufactured by Bausch & Lomb.

Bacterial colonies were then inactivated by adding 0.4% volume/volume (V/V) of a 37% formaldehyde solution (manufactured by Stephens Scientific, or equivalent) and gently stirred at room temperature for 24 hours. Cultures were then stored at 4° C. prior to further processing. The material was tested for inactivation by streaking a blood agar plate with a loopful of culture, incubated anaerobically for 48 hours, and examined for visible growth.

To form the vaccine the killed whole bacteria culture was gently stirred and the adjuvant SuprImm®, manufactured by ImmTech Biologics, L.L.C., was slowly added to the suspension in a final concentration of 20% by volume. The vaccine then had an amount of diluent added thereto. The final formula for use as a vaccine was the following:

| F. necrophorum whole culture | 40,000 ml |
|---|---|
| Saline Diluent | 20,000 ml |
| Adjuvant | 15,000 ml |
| | 75,000 ml |

Example 2

The following example describes a test undertaken to determine the amount of CFUs required to produce an effective vaccine against *F. necrophorum.*

Twenty calves, weighing between 400–600 pounds were randomly assigned to four groups of five calves. The animals were identified by ear tags and were commingled throughout the study. The animals were given feed and water ad libitum and were not given any antibiotics during the trial.

Three lots of bacterin, Vaccines A, B and C, containing antigens from *F. necrophorum* isolate #021496, were prepared and formulated in SuprImm® oil adjuvant, manufactured by ImmTech Biologics, L.L.C. Vaccines A, B, and C contained $3\times10^8$ CFU/dose, $1\times10^8$ CFU/dose, or $3\times10^7$ CFU/dose, respectively. Calves in the first group were vaccinated with Vaccine A. The second group of animals were vaccinated with Vaccine B and the third group were vaccinated with Vaccine C. The fourth group of calves were used as the unvaccinated controls. The animals received subcutaneous vaccinations on day 0 and day 21, 2mL/dose. All of the calves were challenged at day 35 with $2\times10^8$ CFU/ml of an 8 hour virulent culture of *F. necrophorum.* This concentration was previously used to infect similarly aged calves and caused lameness, joint swelling, and abscesses.

Observations then made during the 15 days post-challenge and the clinical signs of disease were scored as follows:

| LAMENESS | JOINT SWELLING | ABSCESSATION |
|---|---|---|
| 0 = None | 0 = None | 0 = None |
| 1 = Mild | 1 = Mild | 1 = Mild |
| 2 = Moderate | 2 = Moderate | 2 = Moderate |
| 3 = Severe | 3 = Severe | 3 = Severe |
| 4 = Holds foot up | | |

The results of the trial are summarized below in Tables 1 through 3.

TABLE 1

Mean Lameness Scores (Post-Vaccination)

| | Day 1 | Day 3 | Day 5 | Day 7 | Day 9 | Day 11 | Day 13 | Day 15 |
|---|---|---|---|---|---|---|---|---|
| Vaccine A | 0 | 0 | 0 | 0 | 0 | 0 | 0 | 0 |
| Vaccine B | 0 | 0.4 | 0.4 | 0.2 | 0 | 0 | 0 | 0 |
| Vaccine C | 0 | 1 | 1.2 | 1.2 | 0.8 | 0.4 | 0 | 0 |
| Vaccine D | 0.4 | 4 | 4 | 4 | 4 | 3.8 | 3.6 | 3.4 |

TABLE 2

Mean Joint Swelling Scores (Post Vaccination)

| | Day 1 | Day 3 | Day 5 | Day 7 | Day 9 | Day 11 | Day 13 | Day 15 |
|---|---|---|---|---|---|---|---|---|
| Vaccine A | 0 | 0 | 0 | 0 | 0 | 0 | 0 | 0 |
| Vaccine B | 0 | 0.2 | 0.4 | 0.2 | 0.2 | 0 | 0 | 0 |
| Vaccine C | 0 | 0.6 | 1.2 | 1.2 | 1 | 0.4 | 0 | 0 |
| Vaccine D | 0.4 | 3 | 3 | 3 | 3 | 3 | 3 | 2.6 |

TABLE 3

Mean Abscess Scores (Post-Vaccination)

| | Day 1 | Day 3 | Day 5 | Day 7 | Day 9 | Day 11 | Day 13 | Day 15 |
|---|---|---|---|---|---|---|---|---|
| Vaccine A | 0 | 0 | 0 | 0 | 0 | 0 | 0 | 0 |
| Vaccine B | 0 | 0 | 0 | 0 | 0 | 0 | 0 | 0 |
| Vaccine C | 0 | 0 | 0 | 1.2 | 0.4 | 0.4 | 0.2 | 0.2 |
| Vaccine D | 0 | 0 | 0 | 0.6 | 2.8 | 3 | 3 | 3 |

Only 1 calf in Group 3 had an increase in rectal temperature whereas all five controls had rectal temperatures of at least 104° C. by the second day post-challenge. None the animals in Group 1 exhibited any clinical signs of lameness, which indicates that the higher dose of vaccine was capable of eliciting complete protection after challenge. In this study, one calf in Group 2 had mild to moderate lameness by the third day post-challenge and three of the calves in Group 3 also showed mild to moderate lameness from day 3 to day 12 post-challenge. In contrast, all of the control animals developed moderate to severe lameness from the second day post-challenge that persisted throughout the trial period. Joint swelling and abscesses were also detected in these calves.

The difference in the number of positive calves in the vaccinated groups indicated that protection is dose dependent. Better protection was shown in calves vaccinated with the vaccine containing $3\times10^8$ CFU/dose, but less protection when the antigen load was only $3\times10^7$ CFU/dose. The results therefore indicate that the minimum preferred protective dose of the vaccine is equal to at least $1\times10^8$ CFU/dose. It is also interesting to note that even though some of the calves in the vaccinated groups showed clinical signs of lameness, they recovered rapidly and none of them were lame at the end of the trial. The results also demonstrate a successful challenge model of infection via inoculation of the interdigital area with a virulent culture of *F. necrophorum* at the appropriate number of organisms.

Example 3

The following example describes a test undertaken to determine the component or components of the *F. necro-*

*phorum* bacteria to be used in order to develop the most effective vaccine against *F. necrophorum* infection.

Twenty calves, weighing 400 lbs. to 600 lbs., were randomly assigned to five groups of four calves. The animals were identified by ear tags and were commingled throughout the study. The animals were given water ad libitum and were not given any antibiotics during the trial.

Four vaccines, A, B, C, and D, were prepared using the method described in Example 1, each vaccine containing a different antigenic component. The antigens were separated by heating the *F. necrophorum* at 56° C. and stirring, causing the capsule and outer membrane protein to slough off. Vaccine A was developed using the capsule and outer membrane protein extracts of *F. necrophorum.* Vaccine B was developed using the toxins secreted by *F. necrophorum.* Vaccine C was developed using only the *F. necrophorum* cells. Vaccine D was developed using the whole cell culture. Calves in the first group were vaccinated with Vaccine A. The second group of animals were vaccinated with Vaccine B and the third group were vaccinated with Vaccine C. The fourth group of calves vaccinated with Vaccine D, and the fifth group of calves were used as the unvaccinated controls. The animals received subcutaneous vaccinations on day 1 and day 21 (2 ml doses with the starting culture equal to $1\times10^8$ CFU/ml). All of the calves were challenged at day 35 with a 5mL dose of a $1\times10^8$ CFU/ml 8 hour virulent culture of *F. necrophorum* via portal skin. This concentration was previously used to infect similarly aged calves and caused liver abscesses.

The livers were harvested 28 days post-challenge and the clinical signs of disease were scored as follows:

| | |
|---|---|
| 0 | no abscess |
| A− | 1 or 2 small abscesses or abscess scars present |
| A | 2 to 4 well-organized abscesses are present, generally under one-inch in diameter |
| A+ | one or more large active abscesses are present along with inflammation of liver tissue surrounding the abscess |

The results of the trial are summarized below.

| Group | Vaccine | Antigen | Abscess Score |
|---|---|---|---|
| 1 | A | capsule + omp | 0, A−, 0, A− (2/4) |
| 2 | B | secreted toxin | A−, 0, 0, A− (2/4) |
| 3 | C | cells only | 0, A, 0, 0 (1/4) |
| 4 | D | complete bacteria | 0, 0, 0, 0 (0/4) |
| 5 | control | control | A+, A+, A+, A+ (4/4) |

The difference in the abscess scores indicated that the best protection is achieved when the complete bacteria whole cell culture is used in the vaccine.

Example 4

A was undertaken to determine the preferred growth period for *F. necrophorum* bacteria. It is believed that the more capsular material present on the cell wall of the bacteria, the more effective the antigenic response in the host. Thus, it is important to monitor the growth of the bacteria, specifically the capsular material, so that a preferred antigenic composition can be produced. Measurements of estimates of the size of the capsular material were made to determine when the greatest amount of capsular material was present. Two separate tests were conducted to verify that the amount of capsular material corresponded to a particular time.

Growth of the bacteria was measured about every two hours over a 24 hour period by mixing one drop of culture, prepared according to the method of Example 1, with one drop of stain, specifically, India Ink. The bacteria and ink were mixed on a slide and then the bacteria/ink mixture was observed through a microscope at 100× magnification. Observations on the bacteria were recorded by scoring capsule size, with the capsule size scored on a scale of 1+ to 4+, with 1+ being the smallest and 4+ being the largest. The results of the trials are summarized below.

| Time | Size |
|---|---|
| 4 hr | 2+ |
| 6 hr | 2+ |
| 8 hr | 3+ |
| 10 hr | 3+ |
| 12 hr | 4+ |
| 14 hr | 4+ |
| 24 hr | 3+ |
| 4 hr | 2+ |
| 6 hr | 2+ |
| 8 hr | 2+ |
| 10 hr | 3+ |
| 12 hr | 4+ |
| 24 hr | 3–4+ |

As can be seen, the greatest capsule size was obtained as a result of a 12 to 14 hour growth period. Capsule size before 12 hours was observed to be smaller. Oppositely, capsule size at 24 hours appeared to be slightly smaller when compared to capsule size at 24 hours. Thus, the greatest antigenic response will likely be achieved when the bacteria is grown between around 12 to 14 hours. This is because it is observed that the capsule is largest at this time. For this reason it is believed to be preferred to harvest the bacteria at the 12 to 14 hour range.

Thus, there has been shown and described a novel vaccine, method for making a vaccine, and method for preventing footrot and liver abscesses in bovines which fulfill all the objects and advantages sought therefore. It is apparent to those skilled in the art, however, that many changes, variations, modifications, and other uses and applications for the subject vaccine and methods are possible, and also such changes, variations, modifications, and other uses and applications which do not depart from the spirit and scope of the invention are deemed to be covered by the invention which is limited only by the claims which follow.

What is claimed is:

1. A vaccine comprised of (a) a killed biotype A (FNN) *Fusobacterium necrophorum* isolate taken from a bovine species member and is identified as ATCC Accession No. PTA-917; and (b) a suitable adjuvant, wherein said *Fusobacterium necrophorum* is killed with formaldehyde.

* * * * *